(12) United States Patent
Shinotsuka et al.

(10) Patent No.: US 10,045,750 B2
(45) Date of Patent: Aug. 14, 2018

(54) RADIATION IMAGE PHOTOGRAPHING SYSTEM

(71) Applicant: Konica Minolta, Inc., Chiyoda-ku, Tokyo (JP)

(72) Inventors: Shin Shinotsuka, Hino (JP); Emiel Visser, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 67 days.

(21) Appl. No.: 15/372,908

(22) Filed: Dec. 8, 2016

(65) Prior Publication Data

US 2017/0156689 A1 Jun. 8, 2017

(30) Foreign Application Priority Data

Dec. 8, 2015 (JP) ................................. 2015-239049

(51) Int. Cl.
*G01T 1/24* (2006.01)
*A61B 6/00* (2006.01)

(52) U.S. Cl.
CPC ............ *A61B 6/461* (2013.01); *A61B 6/4233* (2013.01); *A61B 6/4283* (2013.01); *A61B 6/4405* (2013.01)

(58) Field of Classification Search
CPC ... G01T 1/24; H05G 1/10; H05G 1/32; G21K 1/042; G21K 1/10
See application file for complete search history.

(56) References Cited

U.S. PATENT DOCUMENTS

2012/0163543 A1* 6/2012 Fuse .................... A61B 6/4405
378/96

FOREIGN PATENT DOCUMENTS

JP 2003310595 A 11/2003
JP 2014204783 A 10/2014

* cited by examiner

*Primary Examiner* — Kiho Kim
(74) *Attorney, Agent, or Firm* — Cantor Colburn LLP

(57) ABSTRACT

A radiation image photographing system includes: a radiation generator installed on a round visit cart or a transportable radiation generator; and an FPD cassette including a plurality of radiation detecting elements arrayed two-dimensionally, wherein the radiation image photographing system performs videography by photographing a sequence of multiple radiation images using the FPD cassette, and the radiation image photographing system further includes: a calculation device configured to calculate remaining time before the photography of the sequence of multiple radiation images is finished; and a display device configured to display the calculated remaining time.

8 Claims, 9 Drawing Sheets

RADIATION IMAGE PHOTOGRAPHING SYSTEM

The entire disclosure of Japanese Patent Application No. 2015-239049 filed on Dec. 8, 2015 including description, claims, drawings, and abstract are incorporated herein by reference in its entirety.

BACKGROUND OF THE INVENTION

Field of the Invention

The present invention relates to a radiation image photographing system, and in particular to a radiation image photographing system including a radiation generator installed on a round visit cart or a transportable radiation generator.

Description of the Related Art

As a device for photographing a radiation image which is an alternative to a conventional film/screen, a photostimulable phosphor plate or the like, a flat panel detector (FPD) cassette has been developed. Specifically, as illustrated, for example, in FIG. 2 to be described later, the FPD cassette is configured in such a manner that a plurality of radiation detecting elements 7 is arrayed two-dimensionally (in a matrix), radiation that has passed through an object is converted, by each radiation detecting element 7, into image data D in accordance with its intensity, and the image data D are read.

When radiation is emitted to the conventional film/screen or the photostimulable phosphor plate multiple times, problems such as double exposure and multiple exposure occur, and videography of an object cannot be performed. On the other hand, with the use of the FPD cassette, the read image data D can be saved in a storage unit 23 (refer to FIG. 2 to be described later) within the device, whereby the videography such as kymography of an object can be performed.

As used herein, the kymography means photography that is performed in such a manner that, for example, radiation is emitted to a chest of a patient that is an object multiple times, and as illustrated, for example, in FIG. 10, radiation images (also referred to as frame images or the like in the context of kymography) of a lung field R of the patient in respective time phases T ($T=t_0$ to $t_6$) are acquired. Then, for example, the respective radiation images are further analyzed in a recent attempt to apply the analysis to diagnosis. In the present invention, the videography is not limited to the above-mentioned kymography, and may take on any aspect as long as radiation is emitted to an object multiple times or emitted to an object continuously to photograph a plurality of radiation images.

Meanwhile, in some cases, the videography with the use of the FPD cassette is performed in a well-equipped photographing room. In a case where, for example, a patient cannot come to the photographing room, the videography is likely to be performed in such a manner that a round visit cart (for example, refer to JP 2003-310595 A and JP 2014-204783 A) on which the FPD cassette and the radiation generator or the like are installed is brought into a hospital room in a hospital or the like, and radiation is emitted to a photographing site such as a chest of a patient that is an object multiple times.

Alternatively, the videography is sometimes performed in such a manner that a transportable (i.e., generally referred to as portable) radiation generator 57* illustrated, for example, in FIG. 11 is brought into the hospital room. Although only a main body part of the transportable radiation generator 57* is illustrated in FIG. 11, at the point of use, the transportable radiation generator 57* is fixed to a stand, a leg or the like (not illustrated) and used in this state.

In a case where, for example, the videography is the kymography, the photography of the respective radiation images illustrated in FIG. 10 is performed in such a manner that radiation is emitted from the radiation generator to a patient that is an object for about 20 seconds, during which the patient has to maintain a posture. Therefore, in a case where the patient is unaccustomed to the kymography, the patient does not understand how long he/she has to maintain the posture after the emission of the radiation is started, and the patient is likely to be put under a lot of stress.

In addition, a photographer such as a radiation technologist needs to pay attention by, for example, continuously monitoring whether the posture of the patient is appropriately maintained during the photography. Unlike in the case where the kymography is performed in the photographing room, however, in a case where the round visit cart or the like on which the radiation generator or the like is installed is brought into the hospital room to perform the photography, a person or the like other than the patient is likely to enter an emission field of the radiation. Therefore, the photographer needs to pay further attention so that, for example, the person or the like other than the patient does not enter the emission field of the radiation, and the photographer is likely to be put under a lot of stress.

Furthermore, since the radiation is invisible, the person other than the patient cannot determine, for example, whether the emission of the radiation has been finished. Therefore, for example, another patient in the same hospital room cannot understand whether he/she can come by near the radiation generator, and a helper, a caretaker or the like cannot understand whether he/she can touch the patient that is the object. Consequently, they are subjected to the restriction on the behavior or suffer from the continuous tension for a considerable time, whereby they are also likely to be put under a lot of stress.

As described above, particularly in a case where the FPD cassette and the round visit cart or the like are brought into the hospital room to perform the videography such as the kymography, attention needs to be paid to the fact that the photographing environment is different from that for the photography in the photographing room in the hospital or the like in that the person other than the patient as well as the patient and the photographer such as a radiation technologist is likely to be near the photographing place.

SUMMARY OF THE INVENTION

The present invention has been made in consideration of the above-mentioned points, and an object of the present invention is to provide a radiation image photographing system capable of making a patient that is an object and a person or the like other than the patient precisely recognize whether emission of radiation has been finished.

To achieve the abovementioned object, according to an aspect, a radiation image photographing system reflecting one aspect of the present invention comprises:

a radiation generator installed on a round visit cart or a transportable radiation generator; and an FPD cassette including a plurality of radiation detecting elements arrayed two-dimensionally, wherein the radiation image photographing system performs videography by photographing a sequence of multiple radiation images using the FPD cassette, and the radiation image photographing system further includes:

a calculation device configured to calculate remaining time before the photography of the sequence of multiple radiation images is finished; and a display device configured to display the calculated remaining time.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein:

FIG. 6A is a diagram illustrating an exemplary configuration of the display with a digital representation, and FIG. 6B is a diagram illustrating an exemplary configuration of the display with a progress bar;

DESCRIPTION OF THE PREFERRED EMBODIMENTS

Hereinafter, an embodiment of a radiation image photographing system according to the present invention will be described with reference to the drawings. However, the scope of the invention is not limited to the illustrated examples.

As illustrated, for example, in FIG. 5 to be described later, the following paragraphs describe a case where videography such as kymography is performed with a patient that is an object H lying recumbent on a bed B or the like. However, the present invention can also be applied to a case where, for example, the videography is performed with the patient sitting up on the bed B or the like, or with the patient standing (upright position).

Figure 11:
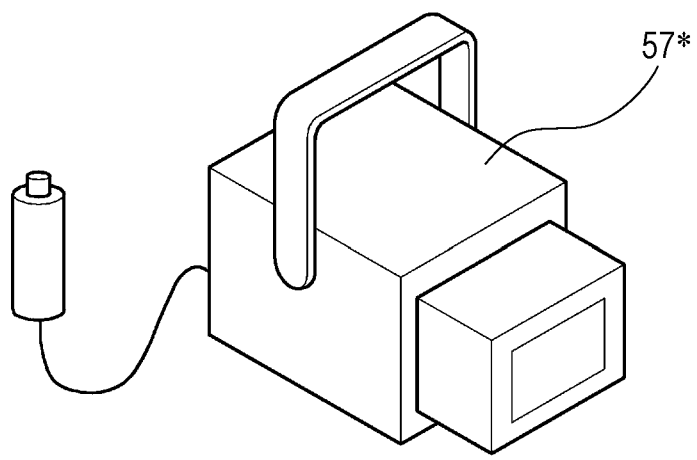
FIG. 11 is a view illustrating an example of a transportable radiation generator.

In addition, the following paragraphs describe a case where a radiation generator 57 installed on a round visit cart 50 (refer to FIGS. 3 and 5 to be described later) is brought into a hospital room to perform the videography. However, as mentioned above, the present invention can also be applied to a case where the transportable radiation generator 57* (refer to FIG. 11) is brought into the hospital room to perform the videography, and this case is also included in the present invention.

[Regarding Configuration of FPD Cassette]

Figure 1:
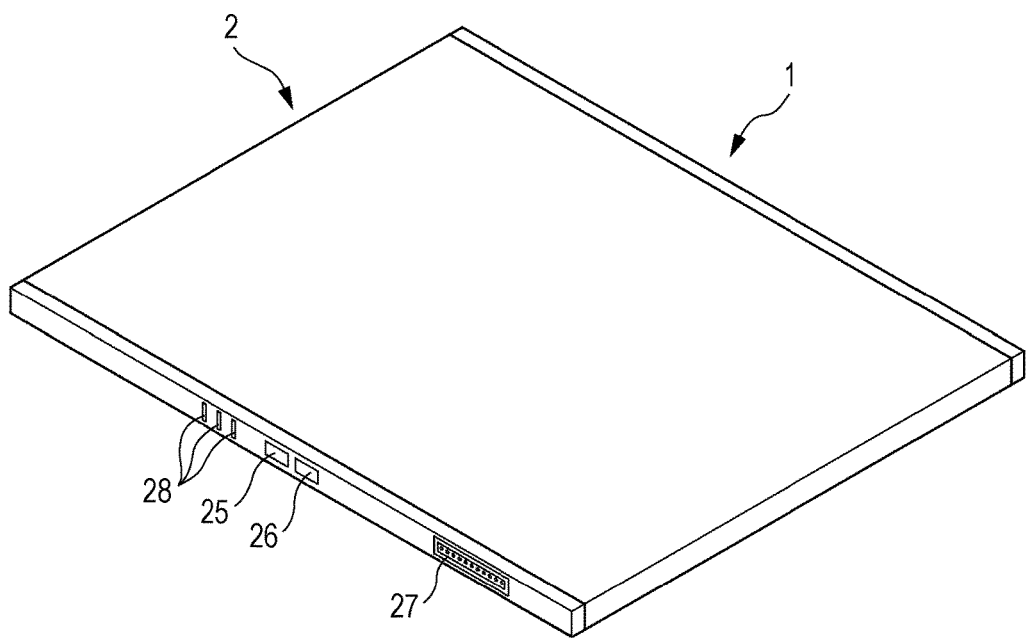
FIG. 1 is a perspective view illustrating an external appearance of an FPD cassette.
Figure 2:
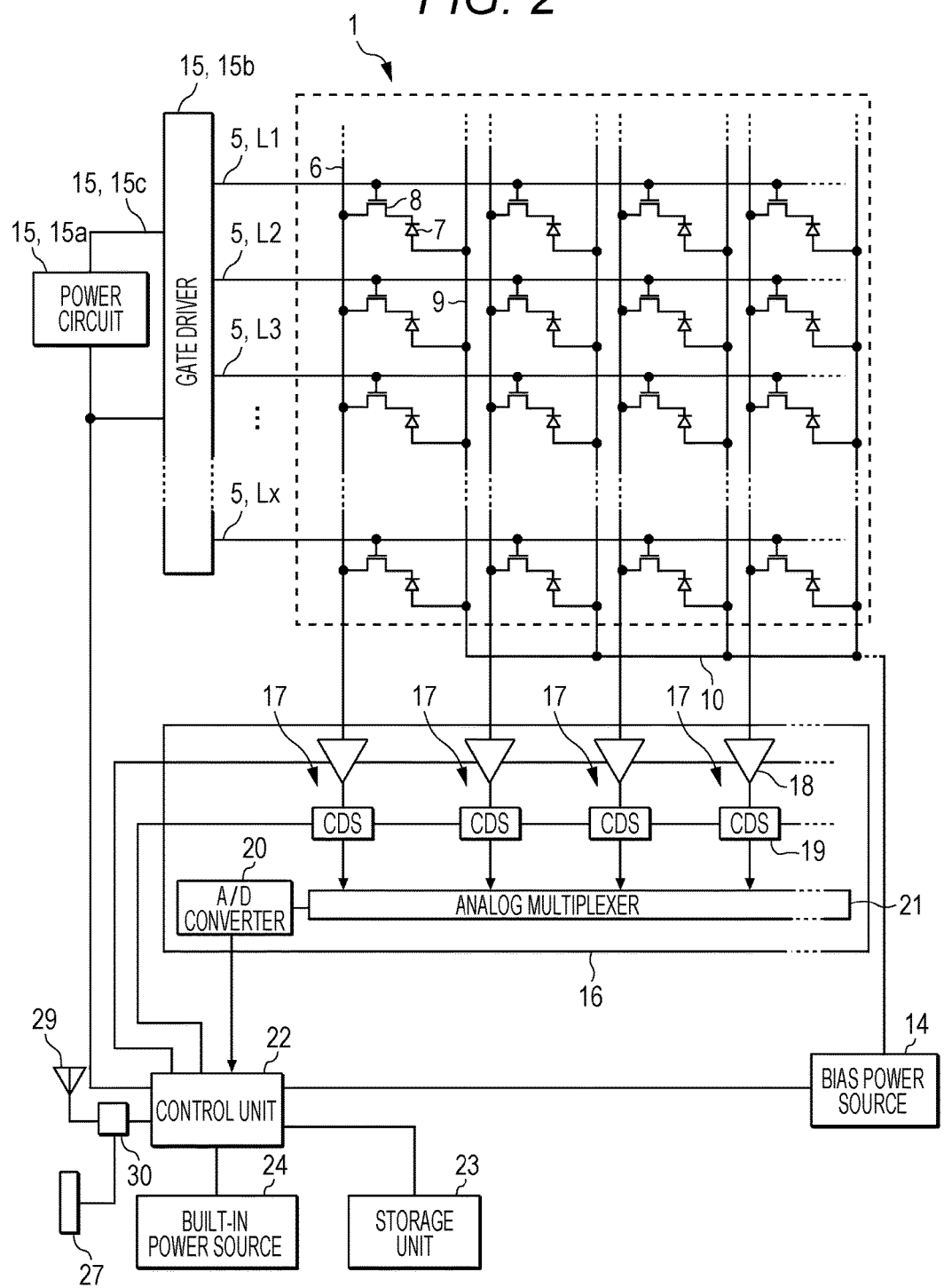
FIG. 2 is a block diagram illustrating an equivalent circuit of the FPD cassette.

First, a configuration or the like of an FPD cassette will be briefly described. FIG. 1 is a perspective view illustrating an external appearance of the FPD cassette, and FIG. 2 is a block diagram illustrating an equivalent circuit of the FPD cassette. As illustrated in FIGS. 1 and 2, the FPD cassette 1 is configured such that a plurality of radiation detecting elements 7 is formed so as to be housed within a housing 2. The plurality of radiation detecting elements 7 is arrayed two-dimensionally (in a matrix) on a sensor substrate (not illustrated).

In FIG. 1, it is illustrated that a power switch 25, a changeover switch 26, a connector 27, and an indicator 28 or the like are arranged on one side surface of the housing 2 of the FPD cassette 1. An antenna 29 (refer to FIG. 2 to be described later) for wirelessly communicating with the outside is provided, for example, on an opposite side surface or the like of the housing 2. An illustration of the antenna 29 is omitted.

As illustrated in FIG. 2, a bias line 9 is connected to each radiation detecting element 7, and a reverse bias voltage is applied from a bias power source 14 to each radiation detecting element 7 through the bias line 9 and a connection line 10 therefor. A thin film transistor (TFT) 8 serving as a switch element is also connected to each radiation detecting element 7, and the TFT 8 is connected to a signal line 6.

In a scanning drive unit 15, an on voltage and an off voltage supplied from a power circuit 15a through wiring 15c are switched in a gate driver 15b, and applied to each line L1 to Lx of a scanning line 5. Each TFT 8 is turned off when the off voltage is applied through the scanning line 5, whereby each TFT 8 shuts off conduction between the radiation detecting element 7 and the signal line 6, and causes a charge to be accumulated in the radiation detecting element 7. Each TFT 8 is turned on when the on voltage is applied through the scanning line 5, whereby each TFT 8 causes the charge accumulated in the radiation detecting element 7 to be released to the signal line 6.

Each signal line 6 is connected to a corresponding read circuit 17 within a read IC 16. During a read process for image data D, the on voltage is sequentially applied from the gate driver 15b to each line L1 to Lx of the scanning line 5. When the TFT 8 is turned on, the charge flows from the radiation detecting element 7 through the TFT 8 and the signal line 6 into the read circuit 17, and a voltage value that depends on the amount of the charge that has flowed into the read circuit 17 is output from an amplifier circuit 18.

A correlated double sampling circuit (described as "CDS" in FIG. 2) 19 reads and outputs the voltage value output from the amplifier circuit 18 as the image data D with an analog value. The output image data D are sequentially transmitted to an A/D converter 20 through an analog multiplexer 21, sequentially converted by the A/D converter 20 into the image data D with a digital value, and sequentially saved in a storage unit 23.

A control unit 22 includes a computer and a field programmable gate array (FPGA) or the like. The computer is configured such that a central processing unit (CPU) (not illustrated), a read only memory (ROM), a random access memory (RAM), an input/output interface and the like are connected to a bus. The control unit 22 may include a dedicated control circuit.

The storage unit 23 and a built-in power source 24 are connected to the control unit 22. The storage unit 23 includes a static RAM (SRAM), a synchronous DRAM (SDRAM), a NAND flash memory or the like. The built-in power source 24 includes a lithium ion capacitor or the like. A communication unit 30 for communicating with the outside through the above-mentioned antenna 29 and the connector 27 using a wireless system or a wired system is also connected to the control unit 22.

In addition, the control unit 22 controls the above-mentioned application of the reverse bias voltage from the bias power source 14 to each radiation detecting element 7, and also controls the operation of the scanning drive unit 15 and the read circuit 17 or the like to cause the scanning drive unit 15 and the read circuit 17 or the like to perform the read process for the image data D from each radiation detecting element 7. The control unit 22 then performs control so that the read image data D are saved in the storage unit 23, or the saved image data D are transferred to the outside through the communication unit 30.

[Regarding Round Visit Cart]

Figure 3:
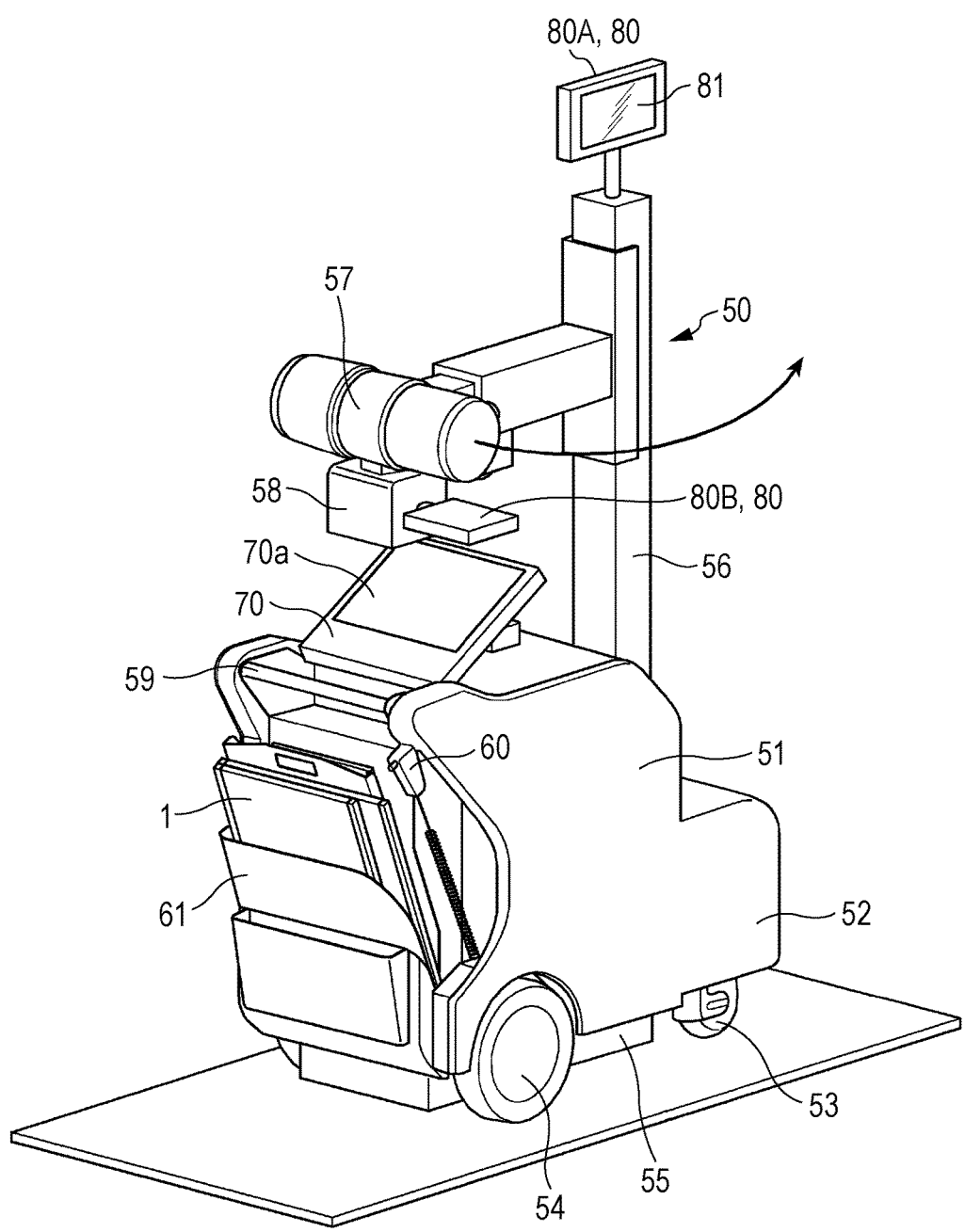
FIG. 3 is a perspective view illustrating an external appearance of a round visit cart according to an embodiment.

Next, a round visit cart according to the present embodiment will be described. FIG. 3 is a perspective view illustrating an external appearance of the round visit cart according to the present embodiment. Hereinafter, the description will be provided on the assumption that a side on which a support 56 of the round visit cart 50 is provided is a front side of the round visit cart 50, and a side on which a handle bar 59 is provided is a rear side of the round visit cart 50.

In the present embodiment, as illustrated in FIG. 3, two front wheels 53 and two rear wheels 54 are provided on the front side of a base 52 of the round visit cart 50 covered with a cover 51 and on the rear side of the base 52, respectively. A drive unit (not illustrated) such as a motor for rotating and driving the rear wheels 54 is embedded in a main body 55 covered with the cover 51. A control unit (not illustrated) or the like of a radiation generator 57 to be described later is also embedded in the main body 55.

On the front side of the base 52 of the round visit cart 50, the support 56 is provided so as to stand in a substantially vertical direction. In the present embodiment, the support 56 is capable of expanding and contracting in an up-down direction. As the support 56 expands and contracts in the up-down direction, the radiation generator 57 attached to an upper end side of the support 56 is also moved up and down. Alternatively, the support 56 may not expand and contract in the up-down direction, and instead, the radiation generator 57 can be configured to go up and down along the support 56. A display device 80A attached to an upper end part of the support 56 will be described later.

In the present embodiment, the support 56 turns around an extending direction thereof (i.e., up-down direction), whereby the radiation generator 57 can turn around the extending direction of the support 56 (refer to an arrow in FIG. 3). Alternatively, the radiation generator 57 is fixed to the support 56, and the support 56 is turned, whereby the radiation generator 57 can be configured to be turned in the above-mentioned manner.

The round visit cart 50 is conveyed with the radiation generator 57 turned to be positioned above the main body 55 (i.e., in the state in FIG. 3). When radiation is emitted from the radiation generator 57, the radiation generator 57 is turned for use by a predetermined angle such as 180° from the state illustrated in FIG. 3.

As the radiation generator 57, a well-known device including a rotating anode (not illustrated) or the like can be used. A collimator 58 or the like for narrowing an emission field of the radiation that is emitted from the radiation generator 57 is attached to a lower side of the radiation generator 57. A display device 80B attached to the collimator 58 will be described later. The display device 80B may be attached to the radiation generator 57. The display device 80B as well as the display device 80A includes a display screen 81. In FIG. 3 and FIG. 5 to be described later, the display screen 81 of the display device 80B is directed downward.

The handle bar 59 that is gripped by a photographer such as a radiation technologist when, for example, the photographer moves the round visit cart 50 is provided on an upper part on the rear side of the round visit cart 50. An exposure switch 60 for instructing the control unit of the radiation generator 57 within the main body 55 to emit the radiation from the radiation generator 57 is detachably attached to a side part on the rear side of the round visit cart 50.

In the present embodiment, a cassette holder 61 into which the FPD cassette 1 or the like can be inserted is provided at a position on the rearmost side of the round visit cart 50. Then, the round visit cart 50 is conveyed to a hospital room with the FPD cassette 1 or the like inserted into the cassette holder 61, whereby it is possible to spare the photographer such as a radiation technologist the trouble of carrying the FPD cassette 1 or the like.

Moreover, a console 70 is arranged on an upper surface of the cover 51 of the round visit cart 50. The console 70 performs processes of, for example, controlling the operation of the FPD cassette 1, subjecting the image data D transferred from the FPD cassette 1 as mentioned above to an image process to generate a radiation image, and displaying the generated radiation image on a display screen 70a.

Figure 4:
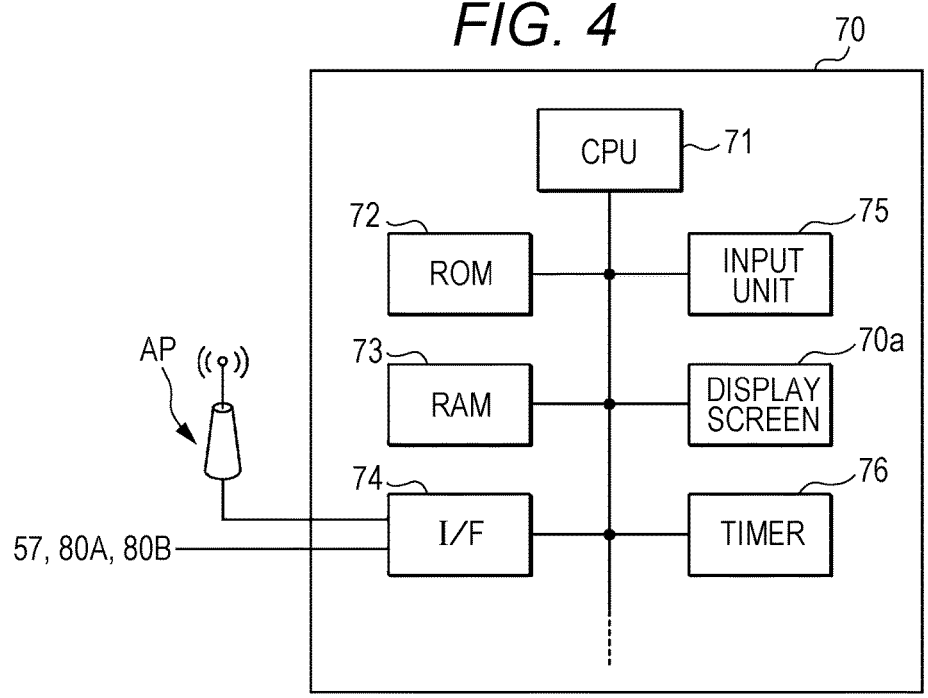
FIG. 4 is a block diagram illustrating a configuration of a console.

In the present embodiment, as illustrated in FIG. 4, the console 70 is configured as a computer in which a CPU 71, a ROM 72, a RAM 73, and an input/output interface 74 or the like are connected to a bus. An input unit 75 and the above-mentioned display screen 70a are connected to the console 70. Examples of the input unit 75 include a keyboard, a mouse, and a touch panel or the like, and the display screen 70a includes a cathode ray tube (CRT) and a liquid crystal display (LCD) or the like.

An access point AP for wirelessly communicating with the FPD cassette 1 or the like, the control unit of the above-mentioned radiation generator 57, and the above-mentioned display devices 80A and 80B or the like are coupled to the console 70 via the input/output interface 74. In the present embodiment, the console 70 includes a timer 76 that measures elapsed time. The timer 76 functions as a calculation device according to an embodiment of the present invention, which will be described later.

In the present embodiment, the console 70 is connected to the control unit of the radiation generator 57 as described above, so that setting for the control unit of the radiation generator 57 such as a tube voltage, a tube current, and photographing time (or mAs value) can be performed on the console 70. However, the console 70 does not necessarily need to be configured in this manner. The photographing time as used herein represents the overall time from the start to the end of the emission of the radiation that is emitted in the form of pulses from the radiation generator 57 or the radiation that is continuously emitted. The same applies to the following. When the radiation is emitted in the form of pulses multiple times, emission time per pulse (i.e., time from the start to the end of the emission of the radiation per pulse) is separately set.

In FIG. 3, it is illustrated that the console 70 is formed integrally with the round visit cart 50. Alternatively, for example, the console 70 including a notebook computer or the like can be configured to be loaded onto the round visit cart 50. As mentioned above, in a case where the transportable radiation generator 57* (refer to FIG. 11) or the like is brought into a hospital room R1 to perform the photography, for example, the console 70 including a notebook computer or the like or the console 70 configured as a mobile terminal is brought into the hospital room R1 together with the transportable radiation generator 57*.

[Regarding Configuration Specific to Present Invention]

Next, a configuration or the like specific to the present invention in the radiation image photographing system according to the present embodiment will be described. Behavior of the radiation image photographing system according to the present embodiment will also be described.

Figure 5:
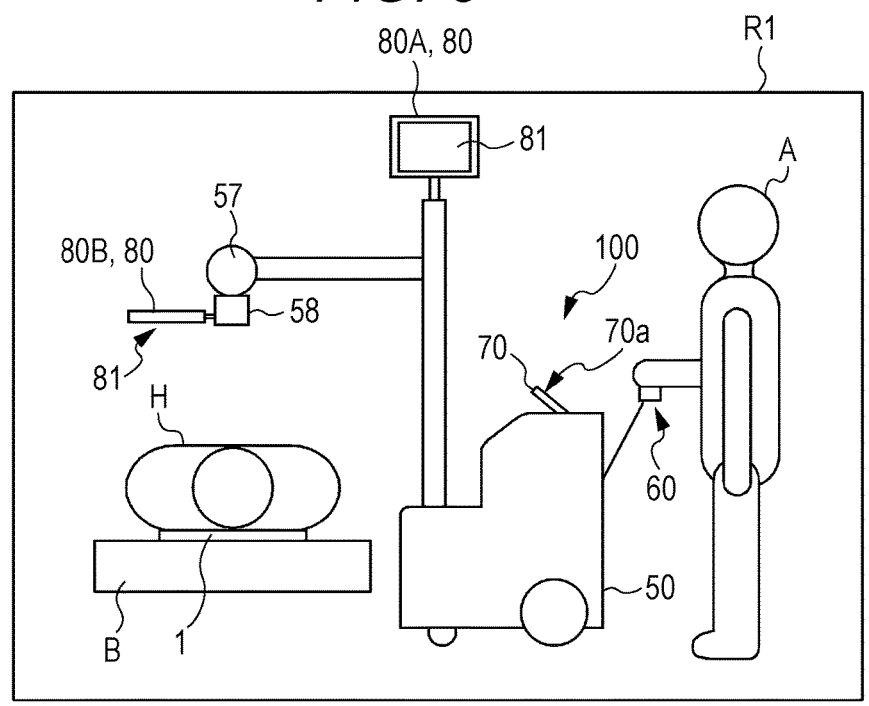
FIG. 5 is a diagram illustrating an overall configuration of a radiation image photographing system according to the present embodiment.

In the radiation image photographing system 100 according to the present embodiment, as illustrated in FIG. 5, the round visit cart 50 is conveyed, for example, to the hospital room R1, and the videography or the like is performed. In FIG. 5, illustrations of another bed B in the hospital room R1 and a person or the like other than a patient that is an object H and a photographer A such as a radiation technologist are omitted. Instead of bringing the radiation generator 57 installed on the round visit cart 50 to perform the photography, a case of bringing the transportable radiation generator 57* (refer to FIG. 11) to perform the photography is also described in a similar manner.

First, a procedure for the normal videography or the like will be described. The photographer A such as a radiation technologist sets the FPD cassette 1 in preparation for the photography. Specifically, for example, the photographer A inserts the FPD cassette 1 between a photographing site (e.g., chest) of the patient that is the object H and the bed B. Next, the radiation generator 57 of the round visit cart 50 is moved up and down or turned, and the round visit cart 50 is brought close to the bed B, whereby the radiation generator 57 is arranged above the object H. Then, positioning operation is performed as necessary. Specifically, for example, a position of the FPD cassette 1 is adjusted, a position adjustment for the radiation generator 57 is performed, or the narrowing degree of the collimator 58 is adjusted.

After the positioning is finished, the photographer A moves to the rear side of the round visit cart 50, operates the exposure switch 60, and emits the radiation from the radiation generator 57 to perform the videography. When the radiation emitted from the radiation generator 57 enters the FPD cassette 1 through the object H, the image data D for one frame are photographed by the FPD cassette 1. Then, the photography is performed multiple times, and the image data D for a plurality of frames are photographed, whereby the videography such as the kymography is performed.

At this time, the FPD cassette 1 can be configured to transfer the image data D to the console 70 each time the photography is performed (i.e., on a frame basis). Alternatively, the FPD cassette 1 can be configured to collectively transfer the image data D for the plurality of frames to the console 70 at the end of a sequence of multiple times of photography.

In the present embodiment, the radiation generator 57 keeps emitting the radiation while the photographer A keeps pressing the exposure switch 60. After the set photographing time elapses, however, the emission of the radiation from the radiation generator 57 is automatically finished even though the photographer A keeps pressing the exposure switch 60. Even though the set photographing time has not elapsed since the start of the emission of the radiation, the emission of the radiation from the radiation generator 57 can be stopped when the photographer A stops pressing the exposure switch 60.

[Regarding Calculation of Remaining Time]

In the radiation image photographing system according to the present embodiment, the console 70 that is the calculation device according to an embodiment of the present invention calculates remaining time $\tau$ before the photography of the sequence of multiple radiation images is finished in the videography.

Hereinafter, the display devices 80A and 80B are sometimes collectively referred to as the display device 80. Hereinafter, in a case where the console 70 functions as the calculation device according to an embodiment of the present invention, the console 70 is represented and described as the calculation device 70. The remaining time $\tau$ before the photography is finished means the remaining time from the start to the end of the emission of the radiation from the radiation generator 57 in a case where the radiation is continuously emitted from the radiation generator 57. In a case where the radiation is emitted from the radiation generator 57 in the form of pulses, the remaining time $\tau$ means the remaining time before the end of the emission of the radiation for photographing the last radiation image.

More specifically, in the present embodiment, when the exposure switch 60 is pressed by the photographer A, and the emission of the radiation from the radiation generator 57 is started, the calculation device 70 causes the control unit of the radiation generator 57 to give notice of the set photographing time Ta, and causes the timer 76 (refer to FIG. 4) to measure the elapsed time t.

Alternatively, the control unit of the radiation generator 57 can be configured to notify the calculation device 70 of the set photographing time Ta in advance. In a case where the setting of the photographing time Ta for the control unit of the radiation generator 57 is enabled to be performed on the console 70, the RAM 73 or the like can be configured to store the photographing time Ta once the photographing time Ta is input to the console 70.

In the above-mentioned case, the calculation device 70 needs to understand that the emission of the radiation from the radiation generator 57 has been started. For example, the control unit of the radiation generator 57 can be configured to, for example, transmit a signal to the calculation device 70 to inform the calculation device 70 when the control unit of the radiation generator 57 causes the radiation generator 57 to start the emission of the radiation.

The calculation device 70 subtracts the elapsed time t measured by the timer 76 from the photographing time Ta set in the control unit of the radiation generator 57 in accordance with the following Formula (1) to calculate the remaining time $\tau$. The calculation device 70 then transmits information of the calculated remaining time $\tau$ to each display device 80.

$$\tau = Ta - t \tag{1}$$

[Regarding Display of Remaining Time]

The display device 80 includes the display screen 81 (refer to FIGS. 3 and 5) including a CRT and an LCD or the like. When the information of the remaining time $\tau$ calculated by the calculation device 70 is transmitted from the calculation device 70, the display device 80 displays the remaining time τ on the display screen 81 based on the information.

Figure 6A:
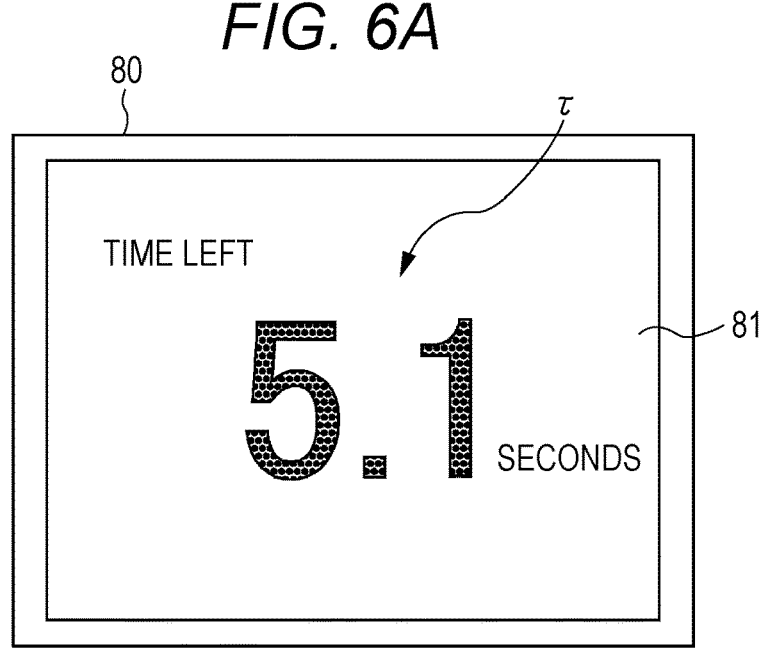
FIGS. 6A and 6B are diagrams illustrating exemplary configurations for displaying remaining time on a display screen, where

As a method of displaying the remaining time τ, as illustrated, for example, in FIG. 6A, the remaining time τ can be digitally displayed. Alternatively, as illustrated, for example, in FIG. 6B, the remaining time τ can be displayed in such a manner that a progress bar 82 is displayed on the display screen 81, the remaining time τ is represented by the length of the bar extending, for example, from the right side to the left, and the length of the bar is displayed so as to be shortened as the remaining time τ is shortened.

Moreover, as illustrated in FIGS. 3 and 5, for example, when the display device 80A is attached to the upper end part of the support 56 of the round visit cart 50, and the remaining time τ is displayed on the display screen 81 of the display device 80A, the patient that is the object H and the person in the hospital room R1 other than the patient can be informed of the displayed remaining time τ.

In addition, as illustrated in FIGS. 3 and 5, for example, when the display device 80B is attached to the radiation generator 57 or the collimator 58, and the display screen 81 of the display device 80B is arranged so as to be directed downward, since the radiation generator 57 and the collimator 58 are arranged above the object H as mentioned above, the patient that is the object H lying recumbent on the bed B can easily see the remaining time τ displayed on the display screen 81 of the display device 80B.

At this time, the display device 80 (80A and 80B) is preferably configured to be capable of changing the direction of the display screen 81. Owing to this configuration, the direction of the display screen 81 of the display device 80 is appropriately changed, whereby the patient that is the object H and the person or the like in the hospital room R1 other than the patient can be enabled to precisely see the remaining time τ displayed on the display screen 81.

Alternatively, the remaining time τ can be displayed on the display screen 70a of the console 70. In this case, the console 70 functions as the display device according to an embodiment of the present invention, and the display screen 70a of the console 70 functions as the display screen of the display device according to an embodiment of the present invention.

Moreover, the display device 80 can also be attached to a place other than the upper end part of the support 56 of the round visit cart 50, the radiation generator 57, and the collimator 58. For example, the display device 80 can be attached to the middle of the support 56 of the round visit cart 50 (position that is not in the upper end part) or to the cover 51. In other words, the display device 80 may be attached to any place on the round visit cart 50 as long as the patient that is the object H, the person in the hospital room R1 other than the patient, and the photographer A can see the place.

Furthermore, in the present embodiment, the description is provided on the premise that the display device 80 is attached to the round visit cart 50, so to speak, in a retrofit manner. Alternatively, the display device 80 can be configured to be formed integrally at a predetermined place on the round visit cart 50.

As described above, since the display device 80 is configured to be installed on the round visit cart 50 in such a manner that the display device 80 is attached to or formed integrally with the round visit cart 50, the display device 80 is conveyed together with the round visit cart 50 when the round visit cart 50 is conveyed to the hospital room R1.

Therefore, the trouble of conveying the display device 80 separately from the round visit cart 50 can be spared.

However, the display device 80 can be provided independently of the round visit cart 50. In this case, for example, the photographer A can arrange the display device 80 at an appropriate place where the display of the remaining time τ on the display screen 81 can be easily seen by the patient that is the object H and the person or the like in the hospital room R1 other than the patient, whereby the patient and the person or the like other than the patient can be precisely informed of the remaining time τ.

[Effect]

As described above, in the radiation image photographing system 100 according to the present embodiment, for the videography such as the kymography performed in such a manner that the radiation is emitted from the radiation generator 57 installed on the round visit cart 50 or the transportable radiation generator 57* (refer to FIG. 11), the remaining time τ before the photography of the sequence of multiple radiation images is finished is displayed on the display device 80.

Since the radiation is invisible, the patient that is the object H and the person who comes in and out of the hospital room R1 other than the patient do not understand by seeing the radiation generator 57 or the like whether the radiation is emitted or the emission has been finished. However, they can understand by seeing the display of the remaining time τ on the display device 80 that the radiation is emitted if the displayed remaining time τ is not zero, and understand the number of seconds left before the end of the emission of the radiation. If the remaining time τ is zero, they can precisely recognize that the emission of the radiation has been finished.

The person or the like other than the patient that is the object H (i.e., another patient or the like in the same hospital room R1 or a helper, a caretaker, or the like for the patient that is the object H) is subjected to the restriction on the behavior, that is, he/she cannot come by near the radiation generator 57 and the object H while the radiation is emitted from the radiation generator 57. The person or the like other than the patient that is the object H is also subjected to such a constraint that he/she cannot touch the patient that is the object H. However, by seeing the display of the remaining time τ on the display device 80, the person or the like other than the patient that is the object H can understand the number of seconds left before the removal of the restriction on the behavior and the constraint, or can recognize the end of the emission of the radiation when the emission of the radiation is finished to precisely understand that the restriction on the behavior and the constraint have been removed.

Therefore, in the radiation image photographing system 100 according to the present embodiment, it is possible to make the person or the like other than the patient that is the object H precisely recognize whether the emission of the radiation has been finished. Consequently, the person or the like no longer feels stress due to the emission of the radiation.

In addition, the patient that is the object H can also recognize by seeing the display of the remaining time τ on the display device 80 the number of seconds left before the end of the necessary maintenance of the posture, and precisely recognize that the emission of the radiation has been finished if the remaining time τ becomes zero. Therefore, in a similar manner, the patient that is the object H no longer feels stress due to the emission of the radiation.

Furthermore, as mentioned above, the photographer A such as a radiation technologist needs to pay attention by, for example, continuously monitoring whether the posture of the patient is appropriately maintained during the photography. However, as described above, since the person or the like other than the patient that is the object H sees the display of the remaining time τ on the display device 80 to precisely recognize the emission of the radiation when the radiation is emitted, he/she does not voluntarily come close to the radiation generator 57 and the object H or touch the patient that is the object H. Consequently, the photographer A such as a radiation technologist no longer needs to pay attention so that, for example, the person other than the patient that is the object H does not enter the emission field of the radiation, whereby the photographer A no longer feels stress.

[Variation of Procedure for Displaying Remaining Time τ]

The above-mentioned embodiment has described the case where the console 70 that is the calculation device includes the timer 76 (refer to FIG. 4), and the console 70 subtracts the elapsed time t measured by the timer 76 from the set photographing time Ta in accordance with the above-mentioned Formula (1) to calculate the remaining time τ, and transmits the information to the display device 80 to cause the display device 80 to display the information.

However, instead of this configuration, for example, the display device 80 can be configured to include a function as the calculation device. Specifically, the display device 80 is configured to include a timer. When the emission of the radiation from the radiation generator 57 is started, an emission start signal is transmitted from the console 70, the control unit of the radiation generator 57 or the like to the display device 80. Then, the display device 80 can be configured, responsive to receiving the emission start signal, to cause the timer to start to measure the elapsed time t, and subtract the elapsed time t measured by the timer from the set photographing time Ta to calculate and display the remaining time τ.

In this case, the set photographing time Ta is transmitted from the console 70, the control unit of the radiation generator 57 or the like to the display device 80 in advance or at the same time as the transmission of the emission start signal. Even in this configuration, advantageous effects similar to those of the above-mentioned embodiment can be obtained. In the same way as in the above-mentioned embodiment, when the calculation device 70 includes the console 70 or the like, and the calculation device 70 is configured to calculate the remaining time τ, such an advantage that each display device 80 does not need to include its own timer is obtained.

[Variation of Calculation Device]

The above-mentioned embodiment has described the case where the console 70 is configured to function as the calculation device according to an embodiment of the present invention. However, instead of this, for example, the control unit of the radiation generator 57 installed on the round visit cart 50 can be configured to function as the calculation device according to an embodiment of the present invention.

As described above, the control unit of the radiation generator 57 is configured to function as the calculation device according to an embodiment of the present invention. Alternatively, as in the above-mentioned embodiment, the console 70 that functions as the calculation device is configured to be formed integrally with the round visit cart 50, or the console 70 including the notebook computer or the like is configured to be loaded onto the round visit cart 50. As a result, the calculation device is conveyed together with the round visit cart 50 when the round visit cart 50 is conveyed to the hospital room R1. Therefore, the trouble of conveying the calculation device separately from the round visit cart 50 can be spared.

Figure 7:
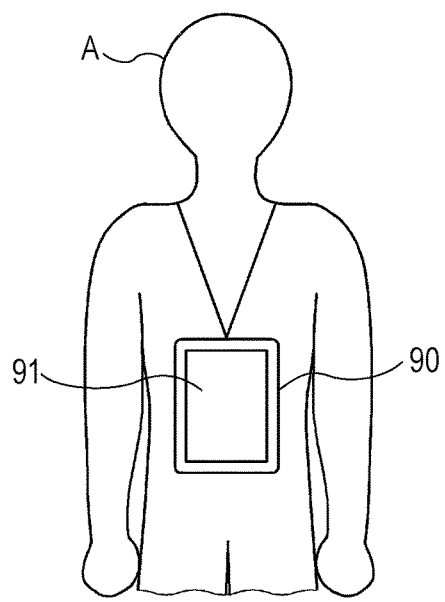
FIG. 7 is a diagram illustrating an exemplary configuration of a mobile terminal carried by a photographer.

As illustrated, for example, in FIG. 7, a mobile terminal 90 can be configured to be carried by the photographer A such as a radiation technologist, and the mobile terminal 90 can be configured to function as the calculation device according to an embodiment of the present invention. Owing to this configuration, the photographer A can operate the mobile terminal 90 at a position apart from the round visit cart 50, and can operate the calculation device according to an embodiment of the present invention even at a position apart from the round visit cart 50.

[Variation of Display Device]

[Variation 1]

Meanwhile, as mentioned above, the console 70 can be configured to function as the display device according to an embodiment of the present invention, and the remaining time τ can be displayed on the display screen 70a of the console 70. Alternatively, the above-mentioned mobile terminal 90 can be configured to function as the display device according to an embodiment of the present invention, and the remaining time τ can be displayed on a display screen 91 of the mobile terminal 90.

At this time, as described above, the mobile terminal 90 can be configured to function as the calculation device according to an embodiment of the present invention, whereby the mobile terminal 90 can be configured to have the functions of both the calculation device and the display device. Alternatively, the console 70 or the like can be configured to function as the calculation device, and the mobile terminal 90 can be configured to function as the display device.

[Variation 2]

Figure 6B:
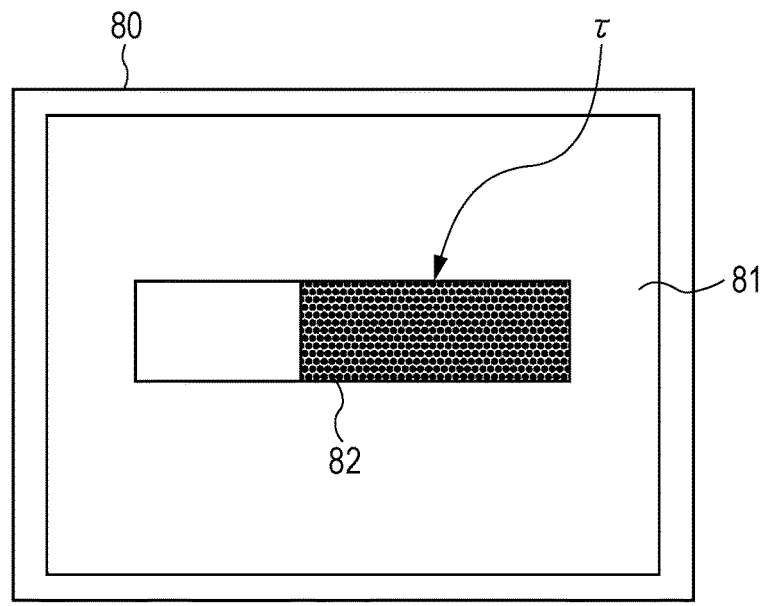

The above-mentioned embodiment and Variation 1 or the like have described the case where the display device 80 includes the display screen 81, and the remaining time τ is displayed on the display screen 81 (refer to FIGS. 6A and 6B). However, the display device 80 does not necessarily need to include the display screen 81, and can be configured, for example, as described in the following respective variations. Even in the configurations in the following respective variations, advantageous effects similar to those of the above-mentioned embodiment or the like can be obtained.

[Variation 2-1]

For example, the display device 80 can include a seven-segment LED or the like, and the seven-segment LED can be configured to be appropriately turned on to display the remaining time τ represented by numbers, an illustration of which is omitted.

[Variation 2-2]

Figure 8A:
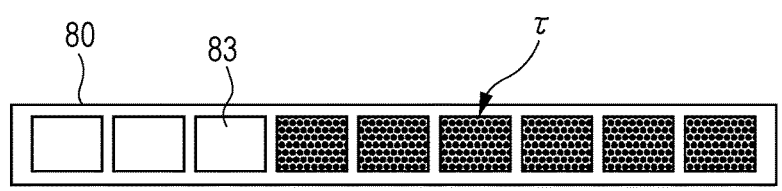
FIGS. 8A and 8B are diagrams illustrating exemplary configurations for displaying the remaining time on a display device, where the display device in FIG. 8A is configured in such a manner that a plurality of light emitting units is aligned in an array, and the display device in FIG. 8B is configured in such a manner that the plurality of light emitting units is distributed.

As illustrated, for example, in FIG. 8A, the display device 80 can be formed in such a manner that a plurality of light emitting units 83 such as LEDs is aligned in an array. In this case, for example, the respective light emitting units 83 are turned on at the time of the start of the emission of the radiation. Then, as the remaining time τ is shortened (in other words, as the elapsed time t elapses), for example, the light emitting units 83 are turned off in order from the left, and the number of light emitting units 83 that are on (light emitting units 83 illustrated by hatching in the drawing) is reduced, whereby the remaining time τ can be displayed.

[Variation 2-3]

Figure 8B:
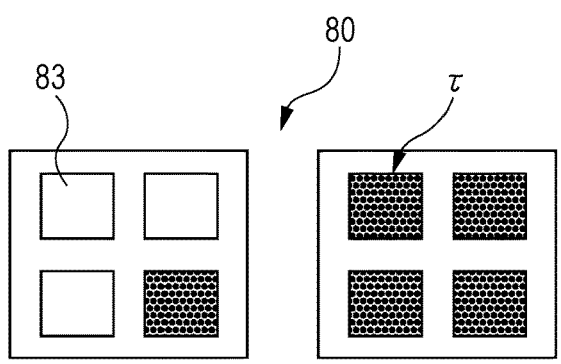

In a case where the display device 80 is formed using the plurality of light emitting units 83, the display device 80 does not necessarily need to be formed in such a manner that the plurality of light emitting units 83 is aligned in the array as illustrated in FIG. 8A. Alternatively, as illustrated, for example, in FIG. 8B, the display device 80 may be configured in such a manner that the plurality of light emitting units 83 is distributed. In this case as well, the remaining time τ can be displayed in such a manner that, for example, the plurality of light emitting units 83 is appropriately turned off in determined order, and the number of light emitting units 83 that are on is reduced.

[Variation 2-4]

The above-mentioned [Variation 2-2] and [Variation 2-3] have indicated the case where, in a way similar to that in the progress bar 82 illustrated in FIG. 6B, the remaining time τ is displayed in such a manner that the number of light emitting units 83 that are on is reduced (corresponding to shortening the length of the bar in the progress bar 82). Alternatively, for example, the remaining time τ can be displayed in such a manner that a position of the light emitting unit 83 to be turned on is changed, i.e., for example, shifted, in the display device 80 (for example, refer to FIGS. 9A to 9C to be described later).

[Variation 2-5]

Meanwhile, in the above-mentioned respective variations, it is assumed that the plurality of LEDs or light emitting units 83 is turned on using the same emission color when the remaining time τ is displayed. Alternatively, the remaining time τ can be displayed in such a manner that the emission color is changed in accordance with the LED or the light emitting unit 83.

[Variation 2-6]

Figure 9A:
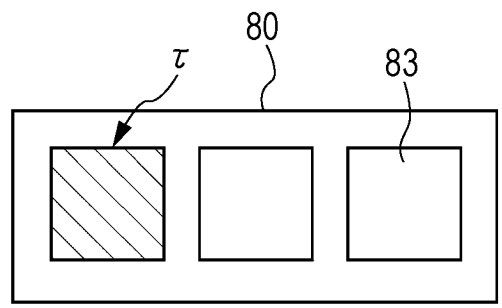
FIGS. 9A to 9C are diagrams illustrating an exemplary configuration of the display device configured to display the remaining time by changing a position of the light emitting unit to be turned on and an emission color.
Figure 9B:
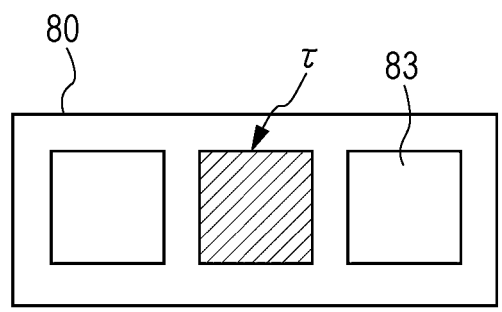
Figure 9C:
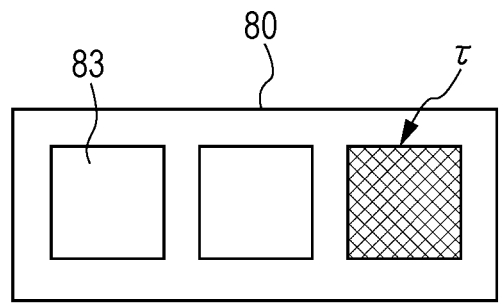
Figure 10:
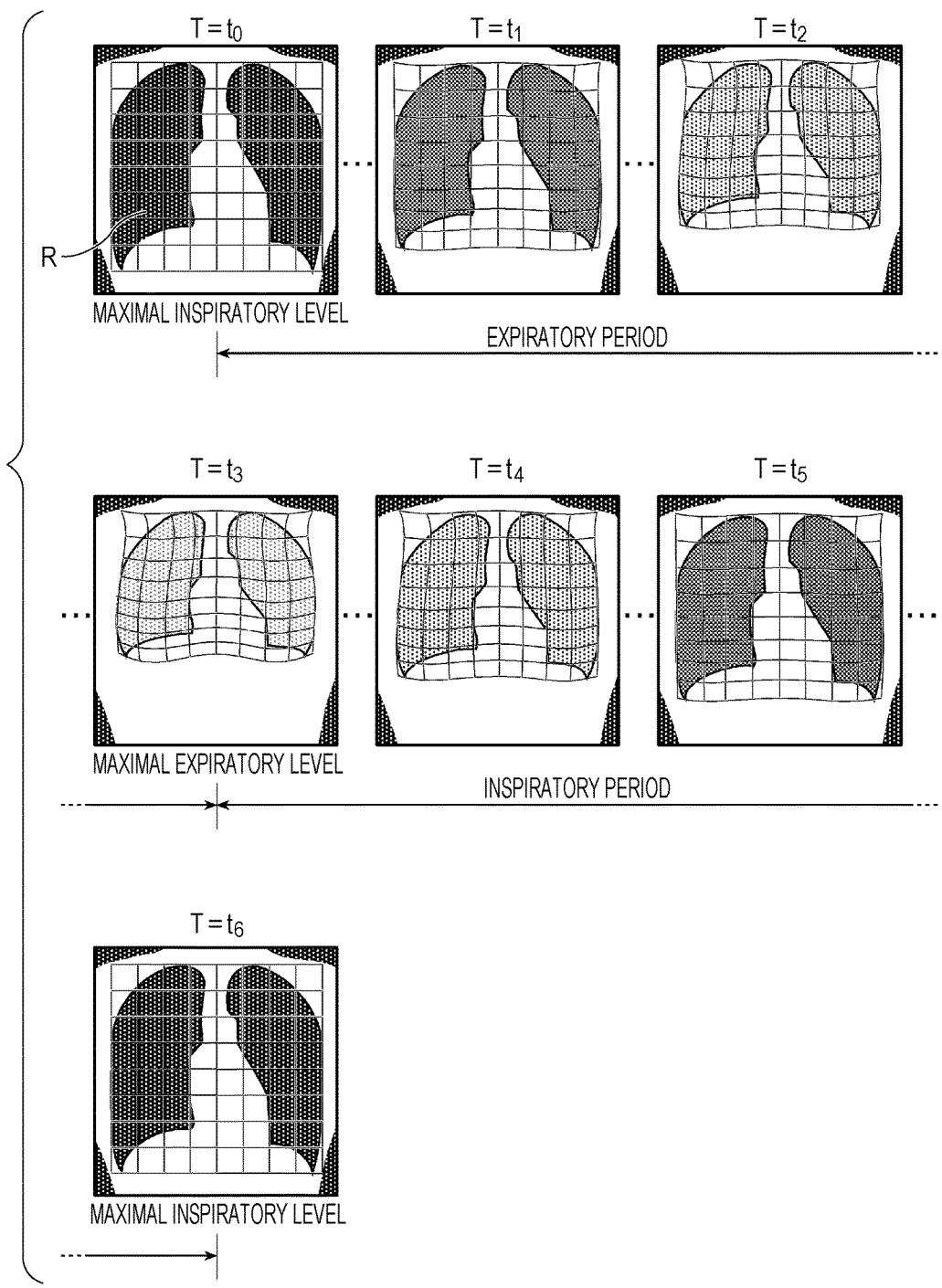
FIG. 10 is a diagram illustrating an example of each frame image photographed in kymography of a chest of a patient.

As illustrated, for example, in FIGS. 9A to 9C, the display device 80 can be configured to display the remaining time τ in such a manner that as the remaining time τ is shortened (in other words, as the elapsed time t elapses), the position of the light emitting unit 83 to be turned on is changed, that is, for example, the light emitting unit 83 to be turned on is shifted, for example, in order from the left, and the emission color for each light emitting unit 83 is changed.

Specifically, in this case, in the same way that a signal of a traffic light is changed in order of blue (green), yellow, and red, as the remaining time τ is shortened, the position of the light emitting unit 83 to be turned on is sequentially shifted to the right, and the emission color is changed. Since some emission colors cannot be used for purposes other than predetermined purposes, emission colors other than the emission colors that can be used only for the predetermined purposes are used as the emission colors for use in the above-mentioned [Variation 2-5] and this [Variation 2-6].

Since the display device 80 is configured as described in the above-mentioned respective variations, even when the display device 80 does not include the display screen 81 unlike in the above-mentioned embodiment, the remaining time τ can be precisely displayed on the display device 80 in a way similar to that in the above-mentioned embodiment.

The display device 80 only needs to be able to precisely inform the patient that is the object H and the person or the like other than the patient of the displayed remaining time τ. The display device 80, therefore, is not limited to the case in the above-mentioned embodiment or each variation.

Needless to say, the present invention is not limited to each embodiment, each variation or the like described above, and can be appropriately changed as long as it does not depart from the gist of the present invention.

Although the present invention has been described and illustrated in detail, it is clearly understood that the same is by way of illustrated and example only and is not to be taken by way of limitation, the scope of the present invention being interpreted by terms of the appended claims.

What is claimed is:

1. A radiation image photographing system comprising:
   a radiation generator installed on a round visit cart or a transportable radiation generator; and
   an FPD cassette including a plurality of radiation detecting elements arrayed two-dimensionally, wherein
   the radiation image photographing system performs videography by photographing a sequence of multiple radiation images using the FPD cassette, and
   the radiation image photographing system further includes:
   a calculation device configured to calculate remaining time before the photography of the sequence of multiple radiation images is finished; and
   a display device configured to display the calculated remaining time.

2. The radiation image photographing system according to claim 1, wherein
   the calculation device causes a timer to measure elapsed time in response to the radiation generator starting to emit radiation, and subtracts the elapsed time measured by the timer from set photographing time to calculate the remaining time.

3. The radiation image photographing system according to claim 1, wherein
   the display device includes a function as the calculation device.

4. The radiation image photographing system according to claim 1, wherein
   the display device is installed on the round visit cart.

5. The radiation image photographing system according to claim 1, wherein
   the display device includes a display screen, and is configured to be capable of changing a direction of the display screen.

6. The radiation image photographing system according to claim 1, wherein
   the calculation device is installed on the round visit cart.

7. The radiation image photographing system according to claim 1, wherein
   the calculation device includes a mobile terminal.

8. The radiation image photographing system according to claim 1, further comprising a mobile terminal including a display screen, wherein
   the mobile terminal displays the remaining time on the display screen.

* * * * *